US 7,056,747 B2

(12) United States Patent
Hudson et al.

(10) Patent No.: US 7,056,747 B2
(45) Date of Patent: Jun. 6, 2006

(54) PROCESS FOR REMOVING ENDOGENOUS VITAMIN B12 AND FOLATE FROM ALBUMIN PREPARATIONS

(75) Inventors: David R. Hudson, Rising Sun, MD (US); Deborah K. Vickery, Landenberg, PA (US); Lisa L. Walton, Smyrna, DE (US); James Strauss, Earleville, MD (US); Daniel Sauers, Newark, DE (US)

(73) Assignee: Dade Behring Inc., Deerfield, IL (US)

( * ) Notice: Subject to any disclaimer, the term of this patent is extended or adjusted under 35 U.S.C. 154(b) by 0 days.

(21) Appl. No.: 10/918,768

(22) Filed: Aug. 13, 2004

(65) Prior Publication Data

US 2006/0036075 A1 Feb. 16, 2006

(51) Int. Cl.
*G01N 33/545* (2006.01)

(52) U.S. Cl. .......................................... 436/505; 422/61

(58) Field of Classification Search ................ 436/505, 436/500, 501; 422/61
See application file for complete search history.

(56) References Cited

U.S. PATENT DOCUMENTS

| 4,046,871 | A |   | 9/1977 | Reckel |
|---|---|---|---|---|
| 4,075,195 | A |   | 2/1978 | Roland |
| 4,339,533 | A |   | 7/1982 | Chu |
| 4,423,154 | A | * | 12/1983 | Gutcho et al. ............... 436/505 |
| 4,473,647 | A |   | 9/1984 | Carpenter et al. |
| 5,185,264 | A |   | 2/1993 | Makela |
| 5,281,536 | A |   | 1/1994 | Wild et al. |
| 5,340,716 | A |   | 8/1994 | Ullman et al. |
| 5,780,594 | A |   | 7/1998 | Carter |
| 5,849,874 | A |   | 12/1998 | van der Laken et al. |
| 5,876,992 | A |   | 3/1999 | De Rosier et al. |
| 6,150,504 | A |   | 11/2000 | van Der Laken et al. |
| 6,294,365 | B1 |   | 9/2001 | De Rosier et al. |
| 6,504,011 | B1 |   | 1/2003 | van Der Laken et al. |
| 6,555,388 | B1 | * | 4/2003 | Boches et al. ............... 436/501 |

OTHER PUBLICATIONS

Ithakissios, D.S., et al. (1977) Use of Protein Containing Magnetic Microparticles in Radioassays. Clinical Chemistry. 23(11): 2072-2079.*

* cited by examiner

Primary Examiner—Robert A. Wax
Assistant Examiner—Marsha Tsay
(74) Attorney, Agent, or Firm—Robert N. Carpenter

(57) ABSTRACT

Processes for removing endogenous Vitamin B12 and folate are provided. The albumin preparations produced by the process are suitable for use as reference control samples in assays for determining these analytes in a test sample. Kits and methods related to the albumin preparations are also provided.

23 Claims, No Drawings

PROCESS FOR REMOVING ENDOGENOUS VITAMIN B12 AND FOLATE FROM ALBUMIN PREPARATIONS

FIELD OF THE INVENTION

The invention relates to albumin preparations, processes for making albumin preparations, and kits and methods relating to the albumin preparations. In particular, the invention relates to albumin preparations having extremely low concentrations of Vitamin B12 and/or folate, to kits including such preparations, and to processes for making such preparations.

BACKGROUND OF THE INVENTION

Albumin is a small globular protein found in several animal body fluids, including serum, cerebrospinal fluid (CSF), interstitial fluid, urine and amniotic fluid. Albumin is the major protein component of plasma, typically comprising more than half of total plasma protein. As such, albumin provides a suitable control in assays for determining analytes in test samples, such as human and animal plasma samples. For example, a series of albumin preparations can be used as reference controls for generation of a standard curve. Each albumin preparation of the series includes a defined concentration of the analyte. Typically, the series includes a preparation having a relatively low concentration of the analyte, a preparation having a relatively high concentration of the analyte, and several preparations having analyte concentrations between the low and high concentrations. To generate the standard curve, the entire series is tested alongside the test samples to generate a series of measurement data that corresponds to the various analyte concentrations evaluated. The standard curve, in turn, allows for determination of the concentration of the analyte in the test samples by extrapolation of a concentration from the standard curve based on measurement data for the test sample.

Because the standard curve provides the basis for extrapolating data for test samples, it is critical to include a series of reference control preparations that include an appropriate range of concentrations of the analyte of interest. The range of analyte concentrations used depends on the desired sensitivity for the assay. For example, the clinical chemistry of some analytes is such that it is desirable for an assay to have the ability to detect extremely low concentrations of the analyte in a test sample. In order for an assay to reliably detect these concentrations, the series of reference controls should include similar low concentrations of the analyte of interest, and desirably includes even lower concentrations.

Vitamin B12 and folate are two analytes for which extremely low serum concentrations can be clinically significant. Serum concentrations of folate may be clinically significant at levels of one to two nanograms per milliliter (ng/ml), while serum concentrations of Vitamin B12 may be clinically significant at levels of 100 picograms per milliliter (pg/ml) or less.

Accordingly, it is desirable to provide suitable reference controls for use in various analyte detection assays, including assays for determining Vitamin B12 and folate in test samples suspected of containing these analytes. Until now, albumin preparations did not have the desired extremely low concentrations of these analytes due at least in part to the presence of endogenous Vitamin B12 and folate in commercially available albumin.

SUMMARY OF EXEMPLARY EMBODIMENTS OF THE INVENTION

The invention provides albumin preparations having extremely low concentrations of both Vitamin B12 and folate. The albumin preparations according to the invention reliably give low level responses in both B12 and folate assays, making these preparations particularly well-suited for use as reference controls in assays for these analytes.

Albumin preparations according to an exemplary embodiment of the invention are produced by a process that includes the steps of contacting an aqueous albumin preparation with a mixture of anion and cation exchange resins, separating a supernatant from the exchange resins once the mixture reaches an initiation pH sufficient to initiate separation of Vitamin B12 and/or folate from the mixture.

The invention also provides kits useful in analytical methods for the determination of an analyte of interest. A kit according to one exemplary embodiment of the invention includes a first albumin preparation having extremely low concentrations of Vitamin B12 and folate. The albumin preparation can be a product of a process according to the invention. The kit of this embodiment also includes at least one additional albumin preparation having concentrations of Vitamin B12 and folate that are higher than those of the first albumin concentration.

The invention also provides methods for determining Vitamin B12 in a test sample suspected of containing Vitamin B12. A method for determining Vitamin B12 according to one exemplary embodiment of the invention comprises determining a concentration of Vitamin B12 in the test sample by comparing measurement data generated for the test sample to a standard curve that is based upon measurement data generated for a first albumin preparation having extremely low concentrations of Vitamin B12 and folate and a second albumin preparation having a concentration of Vitamin B12 that is greater than that of the first albumin preparation.

The invention also provides methods for determining folate in a test sample suspected of containing folate. A method for determining folate according to one exemplary embodiment of the invention comprises determining a concentration of folate in the test sample by comparing measurement data generated for the test sample to a standard curve that is based upon measurement data generated for a first albumin preparation having extremely low concentrations of Vitamin B12 and folate and a second albumin preparation having a concentration of folate that is greater than that of the first albumin preparation.

The invention also provides methods for determining Vitamin B12 and folate in a test sample suspected of containing Vitamin B12 and folate. A method for determining Vitamin B12 and folate according to one exemplary embodiment of the invention comprises determining a concentration of Vitamin B12 in the test sample by comparing measurement data generated for the test sample to a standard curve that is based upon measurement data generated for a first albumin preparation having extremely low concentrations of Vitamin B12 and folate and a second albumin preparation having a concentration of Vitamin B12 that is greater than that of the first albumin preparation. The method according to this exemplary embodiment also comprises determining a concentration of folate in the test sample by comparing measurement data generated for the test sample to a standard curve that is based upon measurement data generated for a first albumin preparation having extremely low concentrations of Vitamin B12 and folate and a second albumin preparation having a concentration of folate that is greater than that of the first albumin preparation.

A more thorough understanding of the invention can be obtained by reviewing the following description of exemplary embodiments of the invention.

DETAILED DESCRIPTION OF EXEMPLARY EMBODIMENTS OF THE INVENTION

The following provides a detailed description of exemplary embodiments of the invention. The description is provided to enable a person having ordinary skill in the art to make and use the invention, and is not intended to limit the scope of the invention or its protection in any manner.

The invention includes processes for removing endogenous folate from albumin preparations. The processes of the invention produce albumin preparations having extremely low concentrations of folate. The processes can also be used to remove endogenous Vitamin B12 from albumin preparations. Preparations made according to the processes of the invention give low level responses in both Vitamin B12 and folate assays, such as Luminescent Oxygen Channeling Immunoassays (LOCI), making the preparations useful as low value reference controls in assays measuring Vitamin B12 and folate. The preparations are particularly well-suited for use in a series of reference controls for generation of a standard curve in these assays.

As used herein, the term "extremely low concentration", and grammatically-related terminology, refers to 0 to about 50 pg/ml in relation to Vitamin B12, and 0 to about 1.0 ng/ml in relation to folate.

In an initial step of a process for removing endogenous Vitamin B12 and folate according to the invention, an aqueous albumin solution is provided. The solution can be prepared in a reaction vessel just prior to conducting the process according to the invention, or can be provided as a previously prepared stock solution. To prepare the aqueous albumin solution, a suitable albumin is provided and is dissolved in water or an aqueous solution. Any suitable albumin can be used, including a serum albumin. Human serum albumin is a suitable albumin for use in the processes according to the invention. To mitigate biohazard concerns associated with handling human serum products, any suitable non-human animal albumin can also be used. The specific albumin chosen will depend on several considerations, including the nature of any test samples with which the resultant albumin preparation will be used. Generally, bovine serum albumin and other non-human serum albumins are considered suitable as controls for assays in which human test samples are evaluated. Accordingly, BSA is advantageous in the practice of the invention.

No matter the origin of the albumin, any suitable form of the chosen albumin can be used. The inventors have noted that a powdered form provides several advantages, including convenient storage, ease of handling, and sufficient stability. Furthermore, a protease free albumin may be particularly advantageous at least because solutions prepared with the albumin are more likely to remain stable over time.

Any suitable water or aqueous solution can be used in preparation of the aqueous serum albumin solution. Examples of suitable waters include distilled water, purified water, and water for injection (WFI).

The aqueous albumin solution can be prepared to have any desired and suitable albumin concentration. The specific concentration chosen will depend on several considerations, including the nature of any diluent used for test samples with which the resultant albumin preparation will be used. For example, if a 6% BSA solution is used as a diluent for test samples in an assay with which the resultant albumin preparation will be used, the initial aqueous albumin solution is advantageously made at substantially the same concentration of BSA.

Following provision of the aqueous albumin solution, the solution is contacted with a mixture of anion and cation exchange resins to produce a mixture that contains the aqueous albumin solution and the mixture of exchange resins. For this step, any suitable exchange resins can be used. For example, Amberlite IRN-78 (anion) and IRN-77 (cation) are suitable exchange resins for use in the methods of the invention. The Amberlite resins are available from Klenzoid Equipment Company, Lansdale Warehouse, 130 Domorah Drive, Montgomeryville, Pa. 18936.

The mixture of exchange resins should include an amount of each resin that is proportional to the percent ion exchange capacity for that particular resin. For example, if the anion exchange resin has a 40% ion exchange capacity and the cation exchange resin has a 60% ion exchange capacity, the mixture of resins should comprise 40% anion exchange resin and 60% cation exchange resin, by weight. Also, the total amount of the anion and cation exchange resins in the mixture of exchange resins should substantially comprise 100% of the mixture of exchange resins.

In another step of the process for making an albumin preparation, the pH of the mixture containing the exchange resins and the aqueous albumin solution is monitored. The pH value determined in this step can be considered an "initiation pH" as another step of the method can be initiated when a desired pH is reached in this step. Advantageously, the pH determination of this step comprises a monitoring of the pH of the mixture over a period of time. The mixture is advantageously agitated during this monitoring step. Once a desired initiation pH is achieved, the exchange resins are separated from the mixture. The initiation pH at which the exchange resins are separated from the mixture can be between about 4 and about 5 for processes using BSA. The specific pH chosen should be one that is sufficient to initiate separation of folic acid from the solution. The inventors have determined that an initiation pH of between about 3.5 and about 5.0 is advantageous in processes for making albumin preparations having desired characteristics. An initiation pH between about 4.0 and 5.0 is particularly advantageous.

The separation step can comprise any suitable separation technique, and the specific technique chosen will depend on various factors, including the form of the ion exchange resins utilized. In one embodiment, the exchange resins are allowed to settle in the reaction vessel and a supernatant fraction is removed from the mixture, such as by pouring the fraction from an upper portion of the reaction vessel. The separation step can include multiple separation steps, if desired. For example, a supernatant fraction can be poured from the reaction vessel, leaving the resins within the vessel, and simultaneously or subsequently exposed to a suitable filtration medium, such as a section of filter paper placed in a funnel. Following separation, endogenous Vitamin B12 and folate remain with the exchange resins.

Once the initiation pH is achieved and the supernatant fraction is obtained, the pH of the supernatant fraction can be adjusted to a level that is sufficient to stabilize the supernatant fraction. The inventors have determined that a pH of between about 4.0 and about 4.5 is suitable, and that any suitable substance for adjusting the pH of a solution can be used. The inventors have determined that 6N HCl is suitable for this purpose. Advantageously, the pH is adjusted to about 4.0 in processes using BSA. The supernatant fraction can be placed in a second reaction vessel and can be agitated during this step, if desired. This adjustment step is considered optional.

Once the desired pH is achieved, the pH of the supernatant fraction is maintained for a period of time. As used herein, the term "maintained," in the context of this step, refers to the active or passive maintenance of the pH of the supernatant fraction at substantially the same level over a period of time. The supernatant can be maintained at this point for any desired period of time, and can be stored for later use. The period of time can be any suitable period of time, and the specific period of time chosen will depend on several considerations, including the immediacy of the need for the albumin preparation. The period of time can be as brief as 1 second or less and as long as several days or more. According to a particular embodiment, a period of time lasting between about 30 and about 90 minutes is appropriate for this step. Advantageously, the supernatant is maintained for a period of time of about 60 minutes. This step can be conducted at room temperature, and can be done with agitation if desired. Also, during this step, the pH of the supernatant can be monitored and adjusted, if necessary, to maintain the pH at the level achieved in the prior step.

If desired, the pH of the supernatant fraction is adjusted to a level that is suitable for the intended use of the resultant albumin preparation. For albumin preparations that will be used in assays for determining analytes in body fluids, a pH that is substantially similar to the particular body fluid is suitable. The inventors have determined that a use pH of between about 7.0 and about 8.0 is suitable for most intended uses, and that any suitable substance for increasing the pH of a solution can be used in this adjustment step. The inventors have determined that both TRIS ((Hydroxymethyl)Aminomethane, available from Sigma) and NaHEPES (N-2-Hydroxyethylpiperazine-N'-2-ethanesulfonic Acid, monosodium salt, available from Research Organics) are suitable for this purpose. Also, the inventors have determined that a pH of about 7.2 is particularly advantageous for processes using BSA.

Once the desired use pH is achieved, the albumin preparation is suitable for use. If desired, the albumin preparation can be exposed to a suitable filtration medium. For this optional step, a 0.2 micron sterile filter has been determined to be suitable in methods using BSA.

Example 1 describes a specific process for removing endogenous Vitamin B12 and folate from an albumin preparation that comprises BSA.

The invention includes albumin preparations produced by the processes according to the invention. The albumin preparations according to the invention have desirable characteristics that make the preparations particularly well-suited for use as reference controls in assays for determining Vitamin B12 and folate in a test sample. Specifically, the albumin preparations give low level responses in Vitamin B12 and folate assays, confirming that the preparations have extremely low concentrations of these analytes.

The albumin preparations of the invention can be evaluated for levels of both Vitamin B12 and folate using any suitable assay for determining these analytes in a sample. One suitable assay technique for evaluating albumin preparations according to the invention for levels of Vitamin B12 and folate is LOCI. This assay measures chemiluminescence generated by a photochemically activatable chemiluminescent compound (PACC) in response to singlet oxygen or another activator. The chemiluminescence generated in a LOCI is directly proportional to the amount of the analyte of interest in a sample because the activator is released from a photosensitive dye that is associated with the analyte through specific binding. LOCI analyses can be conducted in sandwich and competitive immunoassay formats and advantageously include appropriate binding reagents associated with beads. Example 2 describes a general LOCI procedure that is suitable for evaluation of serum albumin preparations according to the invention.

The invention also provides kits useful for determining an analyte in a sample suspected of containing the analyte. The kits according to the invention are useful in the determination of Vitamin B12 and/or folate in a test sample, such as a human or animal test sample. Kits according to the invention comprise at least one albumin preparation having extremely low concentrations of Vitamin B12 and folate. The albumin preparation can be produced by the processes of the invention. The kits according to the invention can include additional optional components, such as one or more albumin preparations containing a predetermined concentration of Vitamin B12 that is greater than that of the albumin preparation having an extremely low concentration of Vitamin B12, one or more albumin preparations containing a predetermined concentration of folate that is greater than that of the albumin preparation having an extremely low concentration of folate, one or more PACCs, and one or more photosensitive dyes.

A kit according to one exemplary embodiment of the invention comprises a first albumin preparation having extremely low concentrations of Vitamin B12 and folate, and at least a second albumin preparation containing a predetermined concentration of Vitamin B12 that is greater than that of the first albumin preparation. The first albumin preparation can be produced by the processes of the invention.

A kit according to another exemplary embodiment of the invention comprises a first albumin preparation having extremely low concentrations of Vitamin B12 and folate, and at least a second albumin preparation containing a predetermined concentration of folate that is greater than that of the first albumin preparation. The first albumin preparation can be produced by the processes of the invention.

A kit according to another exemplary embodiment of the invention comprises a first albumin preparation having extremely low concentrations of Vitamin B12 and folate, and at least a second albumin preparation containing predetermined concentrations of Vitamin B12 and folate that are greater than those of the first albumin preparation. The first albumin preparation can be produced by the processes of the invention.

A kit according to another exemplary embodiment of the invention comprises a first albumin preparation having extremely low concentrations of Vitamin B12 and folate, and a plurality of additional albumin preparations. Each of the plurality of additional albumin preparations contains a predetermined concentration of Vitamin B12 that is greater than that of the first albumin preparation. Advantageously, each albumin preparation of the plurality of additional albumin preparations has a predetermined concentration of Vitamin B12 that is distinct from the predetermined concentration of Vitamin B12 of every other albumin preparation of the plurality of additional albumin preparations.

A kit according to another exemplary embodiment of the invention comprises a first albumin preparation having extremely low concentrations of Vitamin B12 and folate, and a plurality of additional albumin preparations. Each of the plurality of additional albumin preparations contains a predetermined concentration of folate that is greater than that of the first albumin preparation. Advantageously, each albumin preparation of the plurality of additional albumin preparations has a predetermined concentration of folate that is distinct from the predetermined concentration of folate of every other albumin preparation of the plurality of additional albumin preparations.

A kit according to another exemplary embodiment of the invention comprises a first albumin preparation having extremely low concentrations of Vitamin B12 and folate, and a plurality of additional albumin preparations. Each of the plurality of additional albumin preparations contains predetermined concentrations of Vitamin B12 and folate that are greater than those of the first albumin preparation. Advantageously, each albumin preparation of the plurality of additional albumin preparations has predetermined concentrations of Vitamin B12 and folate that are distinct from the predetermined concentrations of Vitamin B12 and folate of every other albumin preparation of the plurality of additional albumin preparations.

A kit according to another exemplary embodiment of the invention comprises, in packaged combination, an albumin preparation according to the invention, an albumin preparation containing a predetermined concentration of Vitamin B12, a first composition comprising a PACC and a member of a specific binding pair. The member of a specific binding pair is able to specifically bind Vitamin B12 and can comprise an antibody, a receptor, or a binding protein. Alternatively, the first composition can comprise a PACC and a Vitamin B12 analog. The kit can include additional optional items as well. For example, the kit can include a photosensitive dye. The photosensitive dye can be in a non-compounded form, or be a portion of a composition comprising the photosensitive dye and a member of a specific binding pair, which can be able to specifically bind Vitamin B12, as above, or can be able to specifically bind another member that is able to specifically bind Vitamin B12. For example, the photosensitive dye can be a portion of a composition that includes the dye and streptavidin. In this example, the composition can specifically bind any biotinylated component, such as a biotinylated member that specifically binds Vitamin B12. In one exemplary embodiment, the photosensitive dye is a portion of a composition comprising the dye and streptavidin, and the kit also includes a biotinylated member that specifically binds Vitamin B12.

A kit according to another exemplary embodiment of the invention comprises, in packaged combination, an albumin preparation according to the invention, an albumin preparation containing a predetermined concentration of folate, a first composition comprising a PACC and a member of a specific binding pair. The member of a specific binding pair is able to specifically bind folate and can comprise an antibody, a receptor, or a binding protein. Alternatively, the first composition can comprise a PACC and a folate analog. The kit can include additional optional items as well. For example, the kit can include a photosensitive dye. The photosensitive dye can be in a non-compounded form, or be a portion of a composition comprising the photosensitive dye and a member of a specific binding pair, which can be able to specifically bind folate, as above, or can be able to specifically bind another member that is able to specifically bind folate. For example, the photosensitive dye can be a portion of a composition that includes the dye and streptavidin. In this example, the composition can specifically bind any biotinylated component, such as a biotinylated member that specifically binds folate. In one exemplary embodiment, the photosensitive dye is a portion of a composition comprising the dye and streptavidin, and the kit also includes a biotinylated member that specifically binds folate.

The invention also provides methods for determining Vitamin B12 in a test sample suspected of containing Vitamin B12. An exemplary method according to the invention includes a step of generating measurement data for a first reference control albumin preparation having extremely low concentrations of Vitamin B12 and folate. The first reference control albumin preparation can be produced according to the processes of the invention. The method also includes a step of generating measurement data for a second reference control albumin preparation having a concentration of Vitamin B12 that is greater than that of the first reference control albumin preparation. Another step of the method includes generating a standard curve that correlates the measurement data for the first and second reference control albumin preparations and the corresponding concentrations of Vitamin B12. The method also includes the steps of generating measurement data for a test sample suspected of containing Vitamin B12, and determining a concentration of Vitamin B12 in the test sample by comparing the measurement data for the test sample to the standard curve and extrapolating a corresponding concentration value.

The invention also provides methods for determining folate in a test sample suspected of containing folate. An exemplary method according to the invention includes a step of generating measurement data for a first reference control albumin preparation having extremely low concentrations of Vitamin B12 and folate. The first reference control albumin preparation can be produced according to the processes of the invention. The method also includes a step of generating measurement data for a second reference control albumin preparation having a concentration of folate that is greater than that of the first reference control albumin preparation. Another step of the method includes generating a standard curve that correlates the measurement data for the first and second reference control albumin preparations and the corresponding concentrations of folate. The method also includes the steps of generating measurement data for a test sample suspected of containing folate, and determining a concentration of folate in the test sample by comparing the measurement data for the test sample to the standard curve and extrapolating a corresponding concentration value.

The invention also provides methods for determining Vitamin B12 and folate in a test sample suspected of containing Vitamin B12 and folate. An exemplary method according to the invention includes a step of generating measurement data for a first reference control albumin preparation having extremely low concentrations of Vitamin B12 and folate. The first reference control albumin preparation can be produced according to the processes of the invention. The method also includes a step of generating measurement data for a second reference control albumin preparation having concentrations of Vitamin B12 and folate that are greater than those of the first reference control albumin preparation. In this exemplary method, the measurement data generated for the first and second reference control albumin preparations include measurement data relating to Vitamin B12 in each preparation and measurement data relating to folate in each preparation. Another step of the method includes generating a standard curve that correlates the Vitamin B12 measurement data for the first and second reference control albumin preparations and the corresponding concentrations of Vitamin B12. Another step of the method includes generating a standard curve that correlates the folate measurement data for the first and second reference control albumin preparations and the corresponding concentrations of folate. The method also includes the steps of generating Vitamin B12 and folate measurement data for a test sample suspected of containing Vitamin B12 and folate. The method also includes the steps of determining a concentration of Vitamin B12 in the test sample by comparing the Vitamin B12 measurement data for the test sample to the standard curve for Vitamin B12 measurement data and extrapolating a corresponding concentration value. The method also includes the steps of determining a concentration of folate in the test sample by comparing the folate measurement data for the test sample to the standard curve for folate measurement data and extrapolating a corresponding concentration value.

In the methods of determining analytes in a test sample according to the invention, the steps of generating measurement data can comprise any suitable technique for generating a measurable signal that relates to the presence of the appropriate analyte in the sample of interest. Examples of suitable techniques include the generation of a measurable fluorescent signal, the generation of a measurable chemiluminescent signal, and the generation of a color change. The specific technique chosen will depend on several considerations, including the nature of the components used in the assay. LOCI is an example of a suitable technique for generating measurement data in the methods of determining analytes according to the invention.

EXAMPLES

Example 1

Process for removing endogenous Vitamin B12 and folate from an albumin preparation that comprises BSA.

The following is a detailed protocol for one process according to the invention. The process is for making a BSA preparation having extremely low concentrations of Vitamin B12 and folate.

1. In an appropriate reaction vessel, dissolve 60.0 grams (g) of protease free BSA powder in 1.0 liter (L) of purified water and mix vigorously.
2. Determine the total quantity of mixed ion exchange resin required by using the following formula:

g of mixed resin required=1.1*(1.0 liters of preparation)*280 g/L

3. Determine the required quantity for the individual anion and cation exchange resins by using the following formulae:

g anion exchange resin=g of mixed resin required*% ion exchange capacity of the anion exchange resin.

g cation exchange resin=g of mixed resin required*% ion exchange capacity of the cation exchange resin.

4. Mix the required quantities of the anion and cation exchange resins in a 2 L beaker.
5. With the BSA solution mixing vigorously, but without foaming, quickly add the entire resin mixture to the BSA solution.
6. Monitor the pH until it reaches 4.5±0.1.
7. Stop mixing the BSA solution and allow the resins to settle in the reaction vessel.
8. Place a section of filter paper in an appropriate-sized funnel and decant the solution into a 1 L beaker.
9. Mix the solution and adjust the pH of the solution to 4.0±0.1 with 6N HCl.
10. Maintain the solution for about 60 minutes at pH 4.0.
11. Adjust the pH of the solution to 7.2±0.1 with either TRIS or NaHEPES.
12. Filter the solution through a 0.2 p sterile filter.

Example 2

LOCI B12 and folate assays suitable for evaluation of albumin preparations according to the invention.

Albumin preparations according to the invention can be evaluated for both B12 and folate levels using LOCI techniques. This example generally describes a LOCI technique suitable for such evaluations.

Two latex bead reagents and a biotinylated analyte receptor are used. One bead reagent, termed sensibead, is coated with streptavidin and contains a photosensitive dye. A second bead reagent, termed chemibead, is coated either with an antibody capable of binding the analyte of interest (sandwich immunoassay format) or an analyte analog (competitive immunoassay format), and contains a chemiluminescent dye.

To conduct the assay, the three reagents are combined in a reaction vessel with the sample of interest (e.g., an albumin preparation according to the invention). If the analyte being determined is present in the sample, a bead-aggregated immunocomplex is formed. The sample is subsequently illuminated at a wavelength at which the photosensitive dye is able to absorb light. If the complex was able to form, meaning that the analyte was present at some level, singlet oxygen is generated by the sensibeads due to the absorption of light. The singlet oxygen diffuses into the chemibeads and triggers a chemiluminescent reaction. Finally, the resultant chemiluminescence is measured and correlated with a standard curve to determine the concentration of the analyte present in the sample.

To measure B12 in a sample according to this technique, chemibeads including either an antibody capable of binding B12 or a B12 analog are used. To measure folate in a sample, chemibeads including either an antibody capable of binding folate or a folate analog are used. For each analyte, the inventors have determined that sensibeads containing a photosensitive dye that is able to absorb light at 680 nm is suitable, and that chemibeads containing a chemiluminscent dye that generates chemiluminescence detectable at 612 nm is suitable.

The foregoing description includes the best mode for practicing the invention as understood by the inventors at the time of filing the application for letters patent. While the best mode has been described in the context of exemplary embodiments, the invention is not limited to this best mode, or any of the exemplary embodiments described herein.

We claim:

1. A process for removing endogenous folate from an albumin preparation, the process comprising:
    providing an aqueous albumin solution containing endogenous folate;
    contacting the aqueous albumin solution with a mixture of anion and cation exchange resins to create a reaction mixture;
    monitoring the pH of the reaction mixture; and
    separating the exchange resins from the reaction mixture to form a supernatant fraction when the pH of the reaction mixture is at an initiation pH sufficient to initiate separation of folic acid from the reaction mixture.

2. The process of claim 1, wherein the aqueous albumin solution comprises human serum albumin.

3. The process of claim 1, wherein the aqueous albumin solution comprises bovine serum albumin.

4. The process of claim 1, wherein the initiation pH is between about 3.5 and about 5.0.

5. The process of claim 1, wherein the initiation pH is between about 4.0 and about 5.0.

6. The process of claim 1, further comprising maintaining the pH of the supernatant fraction at the initiation pH for a period of time.

7. The process of claim 1, further comprising adjusting the pH of the supernatant faction to a use pH that is between about 7.0 and about 8.0.

8. The process of claim 1, wherein the resulting albumin preparation has a folate concentration between 0 and about 1.0 ng/ml.

9. A process for removing endogenous Vitamin B12 from an albumin preparation, the process comprising:
provic an aqueous albumin solution comprising endogenous Vitamin B12;
contacting the aqueous albumin solution with a mixture of anion and cation exchange resins to create a reaction mixture;
monitoring the pH of the reaction mixture;
separating the exchange resins from the reaction mixture to form a supernatant fraction when the pH of the reaction mixture is between about 3.5 and about 5.0.

10. The process of claim 9, wherein the aqueous albumin solution comprises human serum albumin.

11. The process of claim 9, wherein the aqueous albumin solution comprises bovine serum albumin.

12. The process of claim 9, wherein the step of separating the exchange resins from the reaction mixture to form a supernatant fraction is initiated when the pH of the reaction mixture is between about 4.0 and about 5.0.

13. The process of claim 9, further comprising maintaining the pH of the supernatant fraction for a period of time.

14. The process of claim 9, further comprising adjusting the pH of the supernatant faction to a use pH that is between about 7.0 and about 8.0.

15. A method of determining an analyte in a test sample suspected of containing the analyte, the method comprising:
performing an immunoassay technique using a reference control comprising an albumin preparation having a concentration of Vitamin B12 between 0 and about 50 pg/ml and a concentration of folate between 0 and about 1.0 ng/ml.

16. The method of claim 15, wherein the immunoassay technique comprises a Luminescent Oxygen Channeling Immunoassay.

17. A kit for use in an assay for determining an analyte in a test sample, comprising:
a first albumin preparation having a concentration of Vitamin B12 between 0 and about 50 pg/ml;
a second albumin preparation containing a predetermined concentration of Vitamin B12 that is greater than the concentration of Vitamin B12 of the first albumin preparation; and
further comprising a photochemically activatable chemiluminescent compound.

18. A kit for use in an assay for determining an analyte in a test sample, comprising:
a first albumin preparation having a concentration of folate between 0 and about 1.0 ng/ml;
a second albumin preparation containing a predetermined concentration of folate that is greater than the concentration of folate of the first albumin preparation; and
a photoactivatable chemiluminescent compound.

19. The kit of claim 18, further comprising a third albumin preparation containing a second predetermined concentration of folate that is greater than the predetermined concentration of folate of the second albumin preparation.

20. The kit of claim 18, further comprising a member of a specific binding pair that is able to specifically bind folate and a folate analog.

21. The kit of claim 18, further comprising a folate analog.

22. The kit of claim 17, further comprising a Vitamin B12 analog.

23. The kit of claim 17, further comprising a member of a specific binding pair that is able to specifically bind Vitamin B12.

* * * * *

UNITED STATES PATENT AND TRADEMARK OFFICE
CERTIFICATE OF CORRECTION

| | |
|---|---|
| PATENT NO. | : 7,056,747 B2 |
| APPLICATION NO. | : 10/918768 |
| DATED | : June 6, 2006 |
| INVENTOR(S) | : Hudson et al. |

Page 1 of 1

It is certified that error appears in the above-identified patent and that said Letters Patent is hereby corrected as shown below:

In Col. 10, line 6, please delete "0.2 p" and insert --0.2 µ--.

In Claim 7, Col. 11, line 13, please delete "use" before the second "pH".

In Claim 14, Col. 11, line 40, please delete "use" before the second "pH".

In Claim 20, Col. 12, line 34, please delete "and a folate analog".

Signed and Sealed this

Twenty-seventh Day of February, 2007

JON W. DUDAS
*Director of the United States Patent and Trademark Office*